US00PP15540P2

(12) United States Plant Patent
van Rijn

(10) Patent No.: US PP15,540 P2
(45) Date of Patent: Feb. 8, 2005

(54) ***ANTHURIUM* PLANT NAMED 'RIJN200128'**

(50) Latin Name: *Anthurium andreanum*
Varietal Denomination: Rijn200128

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 2 days.

(21) Appl. No.: 10/766,780

(22) Filed: Jan. 28, 2004

(51) Int. Cl.[7] ..... A01H 5/00

(52) U.S. Cl. ..... Plt./365

(58) Field of Search ..... Plt./365

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Anthurium* plant named 'Rijn200128', characterized by its upright and outwardly spreading plant habit; freely clumping growth habit; durable dark green leaves; dark pink to light red-colored spathes with light yellow-colored spadices that are positioned above and beyond the foliage on strong and erect scapes; freely flowering habit; and good inflorescence longevity.

2 Drawing Sheets

Botanical classification/cultivar designation: *Anthurium andreanum* cultivar Rijn200128.

BACKGROUND OF THE INVENTION

The present invention relates to a new and distinct cultivar of *Anthurium* plant, botanically known as *Anthurium andreanum,* and hereinafter referred to by the name 'Rijn200128'.

The new *Anthurium* is a product of a planned breeding program conducted by the Inventor in Schipluiden, The Netherlands. The objective of the program is to create and develop new compact, freely clumping and freely flowering *Anthurium* cultivars with strong roots, dark green leaves, attractive spathe color, and good inflorescence longevity.

The new *Anthurium* originated from a cross by the Inventor on Jun. 21, 1999 of a proprietary selection of *Anthurium andreanum* identified as code number 9515, not patented, as the female, or seed, parent with a proprietary selection of *Anthurium andreanum* identified as code number 9807, not patented, as the male, or pollen, parent. The cultivar Rijn200128 was discovered and selected by the Inventor as a flowering plant within the progeny of the stated cross in a controlled environment in Schipluiden, The Netherlands in April, 2001.

Asexual propagation of the new cultivar by meristem culture in a laboratory in Belgium since April, 2001, has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Rijn200128. These characteristics in combination distinguish 'Rijn200128' as a new and distinct cultivar:

1. Upright and outwardly spreading plant habit.
2. Freely clumping growth habit.
3. Durable dark green-colored leaves.
4. Dark pink to light red-colored spathes with light yellow-colored spadices that are positioned above and beyond the foliage on strong and erect scapes.
5. Freely flowering habit.
6. Good inflorescence longevity.

Plants of the new *Anthurium* can be compared to plants of the female parent, the proprietary selection identified as code number 9515. In side-by-side comparisons conducted in Schipluiden, The Netherlands, plants of the new *Anthurium* differed from plants of the selection 9515 in the following characteristics:

1. Plant habit of plants of the new *Anthurium* was more open than plant habit of plants of the selection 9515.
2. Plants of the new *Anthurium* and the selection 9515 differed in spathe coloration as plants of the selection 9515 had orange-colored spathes.

Plants of the new *Anthurium* can be compared to plants of the male parent, the selection 9807. In side-by-side comparisons conducted in Schipluiden, The Netherlands, plants of the new *Anthurium* differed from plants of the selection 9807 in the following characteristics:

1. Plant habit of plants of the new *Anthurium* was more dense than plant habit of plants of the selection 9807.
2. Plants of the new *Anthurium* had smaller leaves and spathes than plants of the selection 9807.
3. Plants of the new *Anthurium* and the selection 9807 differed in spathe coloration as plants of the selection 9807 had dark red-colored spathes.

Plants of the new *Anthurium* can be compared to plants of the cultivar Pink Love, disclosed in U.S. Plant Pat. No. 11,021. In side-by-side comparisons conducted in Schipluiden, The Netherlands, plants of the new *Anthurium* differed from plants of the cultivar Pink Love in the following characteristics:

1. Plant habit of plants of the new *Anthurium* was more open than plant habit of plants of the cultivar Pink Love.

2. Plants of the new *Anthurium* had larger leaves than plants of the cultivar Pink Love.
3. Spathes of plants of the new *Anthurium* were flatter, thicker and more durable than spathes of plants of the cultivar Pink Love.
4. Plants of the new *Anthurium* had lighter pink-colored spathes than plants of the cultivar Pink Love.

BRIEF DESCRIPTION OF THE PHOTOGRAPHS

The accompanying colored photographs illustrate the overall appearance of the new *Anthurium*, showing the colors as true as it is reasonably possible to obtain in colored reproductions of this type. Colors in the photographs may differ slightly from the color values cited in the detailed botanical description which accurately describe the colors of the new *Anthurium*.

The photograph on the first sheet comprises a side perspective view of a typical flowering plant of the cultivar Rijn200128.

The photograph at the top of the second sheet comprises a close-up view of typical leaf of 'Rijn200128'.

The photograph at the bottom of the second sheet comprises a close-up view of a typical inflorescences of 'Rijn200128'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe ten-month old plants grown in 14-cm containers in Schipluiden, The Netherlands, in a glass-covered greenhouse with average day temperatures of 23° C., average night temperatures of 21° C. and light levels about 6 kilolux.

Botanical classification: *Anthurium andreanum* cultivar Rijn200128.

Parentage:

*Female parent.*—Proprietary selection of *Anthurium andreanum* identified as code number 9515, not patented.

*Male parent.*—Proprietary selection of *Anthurium andreanum* identified as code number 9807, not patented.

Propagation:

*Method.*—By meristem culture.

*Time to initiate roots on a meristem-cultured plant.*—About four weeks at 20 to 24° C.

*Time to develop roots on a meristem-cultured plant.*—About nine months at 20 to 24° C.

*Root description.*—Thick, fleshy, dark pink to cream-colored; lateral roots, thick and abundant.

Plant description:

*Plant shape.*—Upright and outwardly spreading plant habit, inverted triangle, symmetrical.

*Growth habit.*—Freely clumping, bushy and dense growth habit; about seven clumps per plant; moderately vigorous.

*Plant height, from soil level to top of leaf plane.*—About 33 cm.

*Plant height, from soil level to top of inflorescences.*—About 46 cm.

*Plant diameter or spread.*—About 44 cm.

*Foliage description.*—Arrangement: Alternate; simple. Length: About 14.1 cm. Width: About 9.5 cm. Shape: Cordate. Apex: Apiculate. Base: Cordate. Margin: Entire. Texture, upper and lower surfaces: Leathery; glabrous, smooth; durable. Venation pattern: Pinnate. Color: Developing leaves, upper surface: Darker than 146A. Developing leaves, lower surface: 146A. Fully developed leaves, upper surface: 147A to more green than 137A. Fully developed leaves, lower surface: Between 137A and 146A. Venation, upper surface: 144A to 144B. Venation, lower surface: 144B to 144C. Petiole: Length: About 20.7 cm. Diameter, just below geniculum: About 3.5 mm. Diameter, at plant base: About 5 mm. Texture: Smooth, glabrous. Color: 144B. Geniculum length: About 1.8 cm. Geniculum diameter: About 4 mm. Geniculum color: 145A. Wing length: About 2.1 cm. Wing diameter: About 3 mm. Wing color: 144B to 144C slightly tinted with 182D.

Inflorescence description:

*Inflorescence arrangement.*—Spathes with spadices held above and beyond the foliage. Flowering structures arise from leaf axils. Freely and continuous flowering during the autumn in Schipluiden, The Netherlands. Typically about six inflorescences per plant. Inflorescences not fragrant.

*Inflorescence longevity.*—Inflorescences last about two months under winter conditions and about three months under summer conditions; inflorescences persistent.

*Spathe.*—Length: About 6.1 cm. Width: About 8.6 cm. Shape: Broadly cordate with reniform tendencies. Apex: Abruptly acute. Base: Cordate. Margin: Entire. Texture, upper and lower surfaces: Leathery; glabrous, smooth. Aspect: Slightly convex. Color: When developing, front surface: 51A; towards the margins, 51B. When developing, rear surface: 51B; towards the margins, 51D. Fully developed, front surface: 51A to 51B. Fully developed, rear surface: 51B to 51C; towards the margins, 51D to 54D.

*Spadix.*—Length: About 4.9 cm. Diameter: About 7 mm. Shape: Columnar, tapering towards the apex; apex, obtuse. Cross section: Rounded. Aspect: About 10° from vertical. Color: Immature: 16C to 16D; towards the apex, 151D. Mature: 157A.

*Flowers.*—Quantity per spadix: Numerous, about 200. Shape: Rounded. Height: About 0.5 mm. Diameter: About 0.8 mm.

*Reproductive organs.*—Androecium: Anther color: 11D. Amount of pollen: Scarce. Pollen color: 11C. Gynoecium: Stigma shape: Ovoid. Stigma color: 157A. Ovary color: 157A.

*Scape.*—Length: About 33.4 cm. Diameter: About 4 mm. Strength: Strong. Aspect: Erect to slightly outwardly slanted to about 30° from vertical. Color: 144B.

*Seed and fruit.*—Seed and fruit development has not been observed on plants of the new *Anthurium*.

Disease/pest resistance: Under commercial production conditions, plants of the new *Anthurium* have not been observed to be resistant to pathogens or pests common to *Anthurium*.

Temperature tolerance: Plants of the new *Anthurium* have been observed to tolerate temperatures from about 14 to 36° C.

It is claimed:

1. A new and distinct cultivar of *Anthurium* plant named 'Rijn200128', as illustrated and described.

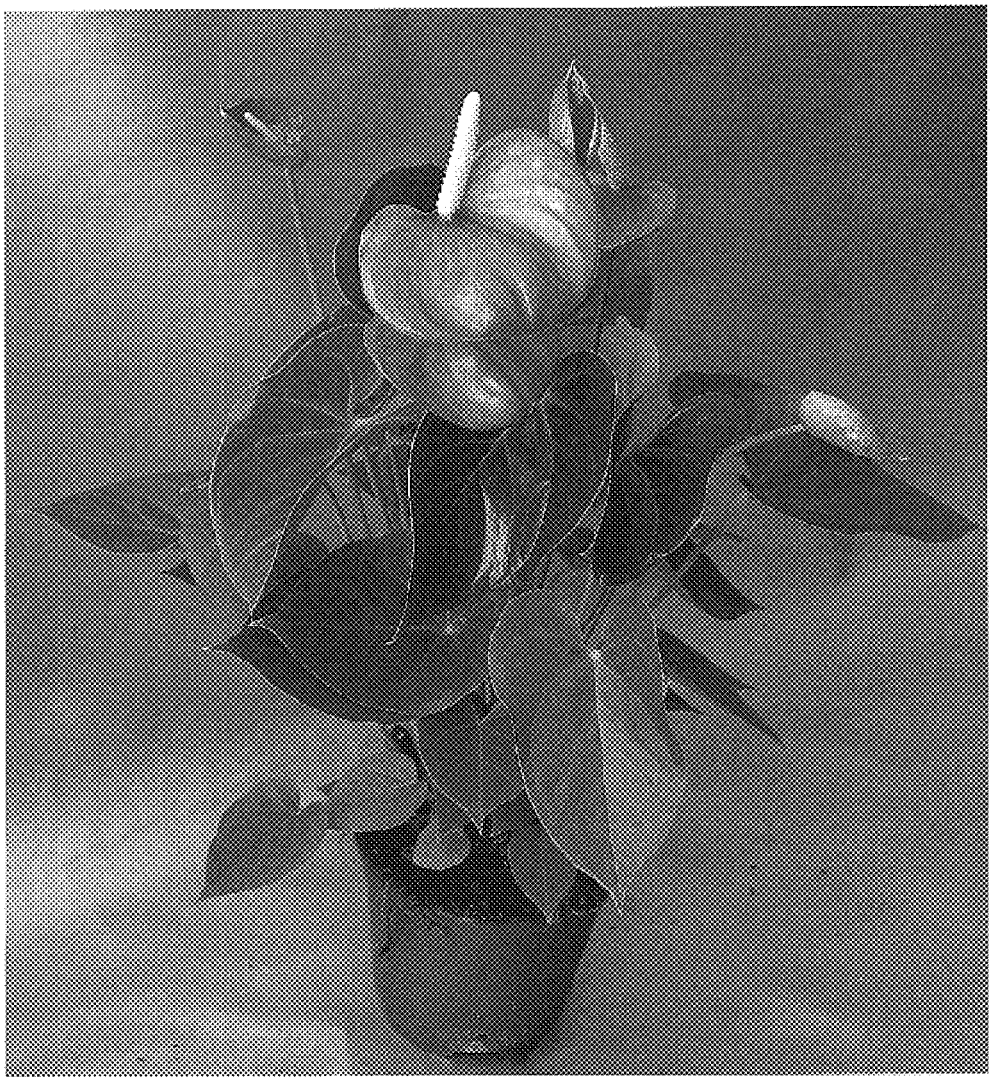

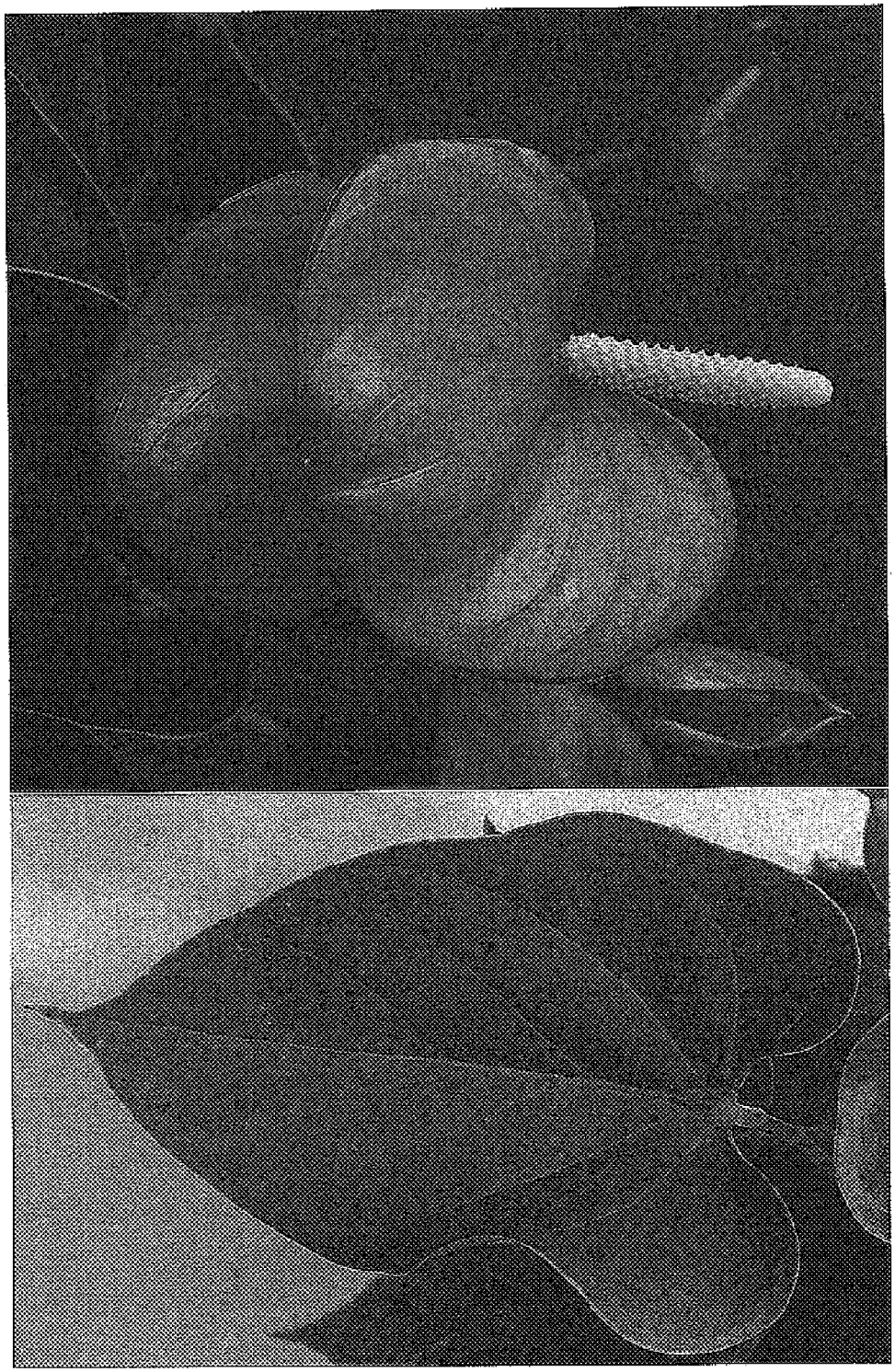

* * * * *